(12) United States Patent
Mertens et al.

(10) Patent No.: US 8,512,409 B1
(45) Date of Patent: Aug. 20, 2013

(54) IMPLANT WITH OUTWARDLY EXTENDING FIXATION ELEMENTS

(75) Inventors: Herbert H. Mertens, San Diego, CA (US); Bassem A. Georgy, San Diego, CA (US); Lex Jansen, Menlo Park, CA (US); Beto Cantu, San Francisco, CA (US)

(73) Assignee: Integral Spine Solutions, Inc., Carlsbad, CA (US)

( * ) Notice: Subject to any disclaimer, the term of this patent is extended or adjusted under 35 U.S.C. 154(b) by 0 days.

(21) Appl. No.: 13/371,180

(22) Filed: Feb. 10, 2012

(51) Int. Cl.
*A61F 2/44* (2006.01)

(52) U.S. Cl.
USPC .................................. 623/17.16; 623/17.11

(58) Field of Classification Search
USPC .... 606/246, 248, 249, 279; 623/17.11–17.16
See application file for complete search history.

(56) References Cited

U.S. PATENT DOCUMENTS

| | | | |
|---|---|---|---|
| 5,458,641 A | 10/1995 | Ramirez Jimenez | |
| 5,522,899 A | 6/1996 | Michelson | |
| 5,554,191 A | 9/1996 | Lahille et al. | |
| 5,609,635 A | 3/1997 | Michelson | |
| 5,653,763 A | 8/1997 | Errico et al. | |
| 5,658,335 A | 8/1997 | Allen | |
| 5,665,122 A | 9/1997 | Kambin | |
| 5,702,391 A | 12/1997 | Lin | |
| 5,776,196 A | 7/1998 | Matsuzaki et al. | |
| 5,800,547 A | 9/1998 | Schafer et al. | |
| 5,800,550 A | 9/1998 | Sertich | |
| 5,893,889 A | 4/1999 | Harrington | |
| 6,102,950 A | 8/2000 | Vaccaro | |
| 6,113,638 A | 9/2000 | Williams et al. | |
| 6,117,174 A | 9/2000 | Nolan | |
| 6,129,763 A | 10/2000 | Chauvin et al. | |
| 6,159,245 A | 12/2000 | Meriwether et al. | |
| 6,176,882 B1 | 1/2001 | Biedermann et al. | |
| 6,179,873 B1 | 1/2001 | Zientek | |
| 6,485,517 B1 | 11/2002 | Michelson | |
| 6,527,803 B1 | 3/2003 | Crozet et al. | |

(Continued)

FOREIGN PATENT DOCUMENTS

| | | |
|---|---|---|
| EP | 0637439 A1 | 2/1995 |
| EP | 0664994 A1 | 8/1995 |

(Continued)

OTHER PUBLICATIONS

International Search Report and Written Opinion of the International Searching Authority for International Application No. PCT/US2013/024791 dated May 7, 2013.

*Primary Examiner* — Eduardo C Robert
*Assistant Examiner* — Christina Negrellrodriguez
(74) *Attorney, Agent, or Firm* — Mintz, Levin, Cohn, Ferris, Glovsky and Popeo, P.C.

(57) ABSTRACT

Described herein are devices, systems and methods for minimally-invasive treating spinal conditions. In one aspect, disclosed is an intervertebral fixation device having a housing sized to be positioned between adjacent inferior and superior vertebrae. The housing includes an internal volume defined by an inferior coupling element, a superior coupling element, and first and second sidewalls. The device includes at least one flexible element coupled to an internal surface of at least one of the inferior or superior coupling elements. The at least one flexible element projects into the internal volume of the housing when in a first configuration. The device includes at least one fixation member coupled to the flexible element and sized to extend through a corresponding aperture in the inferior or superior coupling element.

28 Claims, 11 Drawing Sheets

(56) References Cited

U.S. PATENT DOCUMENTS

| | | |
|---|---|---|
| 6,767,367 B1 | 7/2004 | Michelson |
| 6,972,019 B2 | 12/2005 | Michelson |
| 7,001,432 B2 | 2/2006 | Keller et al. |
| 7,066,961 B2 | 6/2006 | Michelson |
| 2002/0068977 A1 | 6/2002 | Jackson |
| 2002/0138146 A1 | 9/2002 | Jackson |
| 2006/0253201 A1* | 11/2006 | McLuen .................... 623/17.15 |
| 2009/0164016 A1 | 6/2009 | Georgy et al. |
| 2011/0230965 A1 | 9/2011 | Schell et al. |

FOREIGN PATENT DOCUMENTS

| | | |
|---|---|---|
| RU | 2 153 864 C2 | 8/2000 |
| RU | 2 212 865 C1 | 9/2003 |
| RU | 2 285 489 C2 | 10/2006 |
| RU | 2 430 704 C2 | 10/2011 |
| WO | WO-2006116850 A1 | 11/2006 |

* cited by examiner

IMPLANT WITH OUTWARDLY EXTENDING FIXATION ELEMENTS

BACKGROUND

The spinal column includes, among other structures, the bony vertebrae which surround the spinal cord, and the intervertebral discs. In a healthy spine, the discs maintain separation between the vertebrae, promote fluid circulation throughout the spine, and provide a cushioning effect between the bony vertebral structures. A variety of conditions can affect both the vertebrae and intervertebral discs.

Due to the elastic nature of an intervertebral disc, the disc is subject to injury if the disc becomes overstressed, for example, by trauma to the spine, excess body weight, improper mechanical movements and the like. Intervertebral disc injuries and other abnormalities result in serious back pain and physical disability and are often chronic and difficult to treat. Such abnormalities include, but are not limited to, localized tears or fissures in the disc annulus, localized disc herniations with contained or escaped nuclear extrusions, and circumferential bulging discs. Discs also experience degeneration over time which can accelerate these problems.

One of the common disc problems that occur when the entire disc bulges circumferentially about the annulus rather than in specific, isolated locations. This may occur for example, when over time, the disc weakens, bulges, and takes on a "roll" shape. The joint may become unstable and one vertebrae may eventually settle on top of another. This problem typically continues to escalate as the body ages, and accounts for shortened stature in old age. Osteophytes may form on the outer surface of the disc and further encroach upon the spinal canal and nerve foramina. This condition is called spondylosis.

Traditional non-surgical treatments of disc degeneration and abnormalities include bed rest, pain and muscle relaxant medication, physical therapy or steroid injection. Such therapies are directed primarily at pain relief and potentially delaying further disc degeneration. Eventually, most non surgical treatments fail In many cases surgical alternatives, often spinal fusion, may be the only option. Spinal fusion methods are aimed at causing the vertebrae above and below the injured disc to grow solidly together forming a single piece of bone. This procedure is carried out with or without discectomy (surgical removal of the disc). Another procedure, endoscopic discectomy, involves removing tissue from the disc percutaneously in order to reduce the volume of the disc, thereby reducing impingement of the surface of the disc on nearby nerves.

SUMMARY

The subject matter described herein provides many advantages. For example, the current subject matter is related to devices and systems that can be positioned in a minimally-invasive manner to fixate and treat spinal conditions.

In one aspect, disclosed herein is an intervertebral fixation device having a housing sized to be positioned between adjacent inferior and superior vertebrae. The housing includes an internal volume defined by an inferior coupling element, a superior coupling element, and first and second sidewalls. The device includes at least one flexible element coupled to an internal surface of at least one of the inferior or superior coupling elements. The at least one flexible element projects into the internal volume of the housing when in a first configuration. The device includes at least one fixation member coupled to the flexible element and sized, to extend through a corresponding aperture in the inferior or superior coupling element.

The fixation member can be wholly contained within the internal volume of the housing when the flexible element is in the first configuration. The fixation member can extend at least in part through the aperture when the flexible element is in a second configuration. The fixation member can project into an adjacent endplate when the flexible element is in the second configuration. The device can further include a plurality of flexible elements. The device can further include a plurality of fixation members. The inferior and superior coupling elements can be parallel to one another. The inferior and superior coupling elements can be non-parallel to one another. At least one of the inferior and superior coupling elements can include a textured outer surface. The housing can further include a proximal opening through which the internal volume is accessible. The device can further include a delivery device having a distal end region configured to extend into the internal volume through the proximal opening and couple to the housing. The flexible element can be deployed using the delivery device extending through the proximal opening.

In another aspect, disclosed is a method of treating a spinal disorder in a patient with an intervertebral fixation device. The method includes accessing a disc space between an inferior vertebra and a superior vertebra; advancing an intervertebral fixation device positioned on a delivery device into a disc space between the inferior and superior vertebrae. The intervertebral fixation device includes a housing having an internal volume defined by an inferior coupling element, a superior coupling element, and first and second sidewalls; at least one flexible element coupled to an internal surface of at least one of the inferior or superior coupling elements, wherein the at least one flexible element projects into the internal volume of the housing when in a first configuration; and at least one fixation member coupled to the flexible element and sized to extend through a corresponding aperture in the inferior or superior coupling element. The method also includes deploying the at least one flexible element to a second configuration with the delivery device such that the fixation member extends at least in part through the aperture.

Accessing a disc space between an inferior vertebra and a superior vertebra can include inserting an access device through Kambin's triangle into the disc space. The method can further include using the access device to prepare a vertebral endplate of the inferior or the superior vertebrae. Advancing an intervertebral fixation device positioned on a delivery device into a prepared disc space can include inserting the intervertebral fixation device through the access device into the disc space. The fixation member can be wholly contained within the internal volume of the housing when the flexible element is in the first configuration. The fixation member can project into a vertebral endplate of the inferior or the superior vertebrae when the flexible element is in the second configuration. The housing can further include a proximal opening through which at least a distal end region of the delivery device can extend into the internal volume. Deploying the at least one flexible element can include withdrawing the delivery device from the internal volume through the proximal opening. The distal end region of the delivery device can include a flange that presses against the flexible element urging the fixation member through the aperture when the delivery device is withdrawn in a proximal direction. The method can further include injecting bone growth stimulating material into the internal volume of the housing through the proximal opening. The intervertebral fixation device can further include a plurality of flexible elements. The intervertebral fixation device can further include a plurality of fixation members.

In another aspect, disclosed is a kit for use in treating a spinal disorder. The kit includes an intervertebral fixation device and a delivery device. The intervertebral fixation device includes a housing sized to be positioned between adjacent inferior and superior vertebrae. The housing includes a proximal opening to an internal volume defined by an inferior coupling element, a superior coupling element, and first and second sidewalls. The intervertebral fixation device includes at least one flexible element coupled to an internal surface of at least one of the inferior or superior coupling elements, wherein the at least one flexible element projects into the internal volume of the housing when in a first configuration. The intervertebral fixation device also includes at least one fixation member coupled to the flexible element and sized to extend through a corresponding aperture in the inferior or superior coupling element. The delivery device includes a proximal, elongate portion and a distal end region. The distal end region is configured to extend into the internal volume through the proximal opening and couple to the housing.

The delivery device can be pre-coupled to the intervertebral fixation device. The kit can further include bone growth stimulating material. The kit can further include an access and distraction device, wherein the intervertebral fixation device is configured to be delivered through a working channel of the access and distraction device.

More details of the devices, systems and methods for implantation are set forth in the accompanying drawings and the description below. Other features and advantages will be apparent from the description and drawings, and from the claims.

BRIEF DESCRIPTION OF THE DRAWINGS

These and other aspects will now be described in detail with reference to the following drawings. Generally speaking the figures are not to scale in absolute terms or comparatively but are intended to be illustrative of claimed features. Also, relative placement of features and elements may be modified for the purpose of illustrative clarity.

DETAILED DESCRIPTION

Described herein are devices, systems and methods for minimally-invasive access to the disc space to restore and improve the disc height and achieve fusion of adjacent discs. The devices, systems and methods described herein can be used to treat spinal diseases, disc diseases, and degenerative disc diseases including fusion, disc repair and disc height restoration.

Figure 1A:
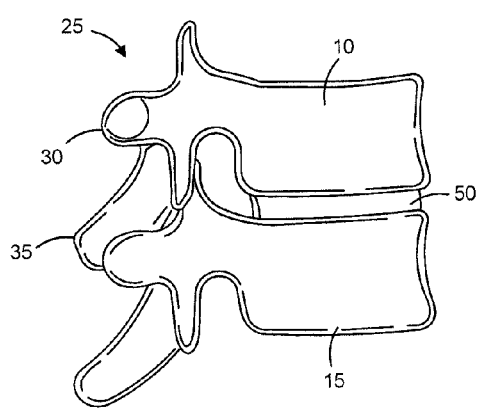
FIG. 1A is simplified, sagittal view of a vertebrae pair.
Figure 1B:
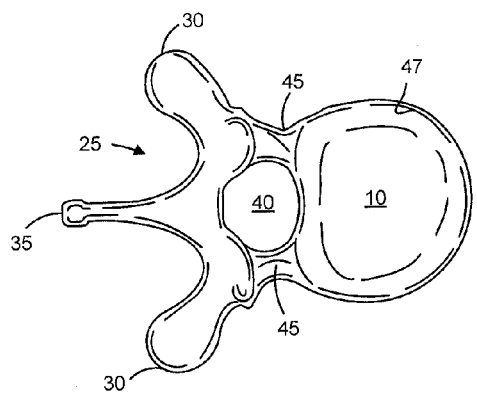
FIG. 1B is a simplified, sectional axial view of a vertebra.

FIG. 1A is a simplified sagittal view of a vertebrae pair 10, 15. FIG. 1B is a simplified, sectional axial view of the vertebrae 10 of the vertebrae pair shown in FIG. 1A. Each vertebra 10, 15 includes lamina 25, transverse processes 30, a spinous process 35, central canal 40, and pedicles 45. A disc 50 comprised of an annulus and disc nucleus (not shown) is located between the vertebrae pair 10, 15 where the vertebrae pair 10, 15 and disc 50 form a coupled articulated jointed bony interface at the location of a hardened outside endplate 47 of the vertebrae.

The devices, systems and methods described herein are generally designed for minimally-invasive procedures including "mini-open" procedures characterized by small incisions, percutaneous procedures, or a combination thereof. The devices, systems and methods described herein can be deployed through a variety of access channels. It should be appreciated that the devices described herein can be inserted laterally, anteriorly, posteriorly and/or posterior-laterally. The devices, systems and methods described herein are generally used under fluoroscopic guidance.

Figure 2:
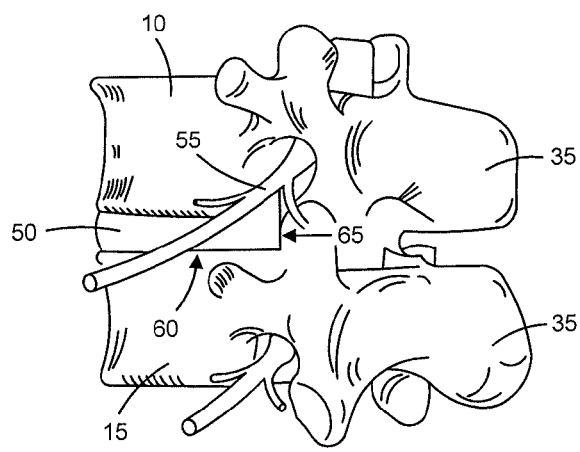
FIG. 2 is a simplified, sagittal view of a vertebrae pair illustrating Kambin's Triangle.

As will be described in more detail below, instrumentation described herein can be introduced between the traversing and exiting nerves in an area known as Kambin's Triangle (see FIG. 2). Kambin's Triangle is a site of surgical access for posterolateral discectomy. Kambin's Triangle is formed over the dorsolateral disc with the hypotenuse being the exiting root 55 (the root that leaves the spinal canal just cephalad (above) the disc, the base being the superior border 60 of the caudal vertebra 15, and the height being the traversing nerve root 65 (the root that leaves the spinal canal just caudad (below)). The vital structures involved with the posterior or posterior/lateral approaches are the nerve roots. The triangle can be enlarged by retracting the traversing nerve root medially. If retraction is done too vigorously, however, retraction injuries may occur and serious complications such as nerve root sleeve tear may result, causing spinal fluid leakage, nerve root injury, avulsion and even spinal cord injury.

The figures illustrate the anatomic landmarks in the spine and access through the vertebrae to the intervertebral disc space in schematic. Those skilled in the art will appreciate that actual anatomy include anatomical details not shown in the figures. It should also be appreciated that although the drawings illustrate the devices implanted in the thoracic vertebrae, that the devices and methods can be used along entire spine including cervical, thoracic and lumbar levels.

The implants described herein can be used to restore and stabilize a portion of a spine following partial or full removal of an intervening disc. The implants can restore a normal separation distance between vertebrae adjacent to the degenerated disc and can restore increased cross-sectional area and volume to the central canal, lateral recess, and neuroforamina. The implants described herein can be used independently or in conjunction with other systems or devices to provide stability to the spine. For example, the implants described herein can be delivered using access, dilator and retractor tools as described in co-pending application Ser. No. 13/371,141, entitled "Delivery Device With Interior Dilation Element Channel," filed on the same day herewith, and which is incorporated by reference in its entirety. Similarly, the implants described herein can be used in conjunction with the fixation and stabilization devices and methods described in co-pending application publication no. 2009/0164016, entitled "Device and Method for Orthopedic Fracture Fixation," filed Dec. 18, 2008, and which is incorporated by reference herein its entirety.

Figure 3A:
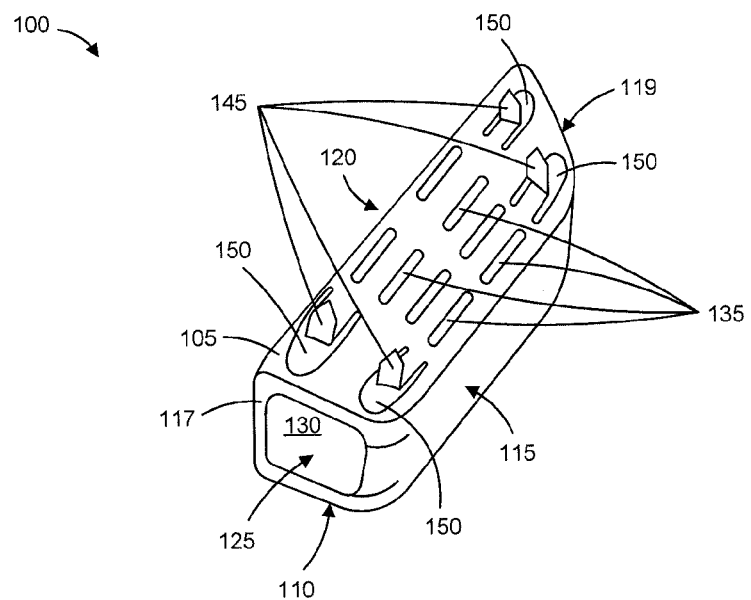
FIG. 3A is a perspective view of an implant in a deployed state.

FIG. 3A is a perspective view of an implant 100. The implant 100 generally includes superior and inferior surfaces 105, 110 configured to engage and fuse with the endplates of the respective superior and inferior vertebrae. The superior and inferior surfaces 105, 110 can be connected by two sidewalls 115, 120 and have a proximal end 117 and a distal end 119. The superior surface 105, inferior surface 110, sidewalls 115, 120, proximal end 117 and distal end 119 create a relatively open design of the implant 100 and relatively large size to the internal volume 130 for material to be inserted as will be described in more detail below. At least the proximal end 117 can have an opening 125 through which the internal volume 130 of the implant 100 can be accessed. The opening 125 also can be used to deliver and deploy the device as will be described in more detail below.

Figure 4A:
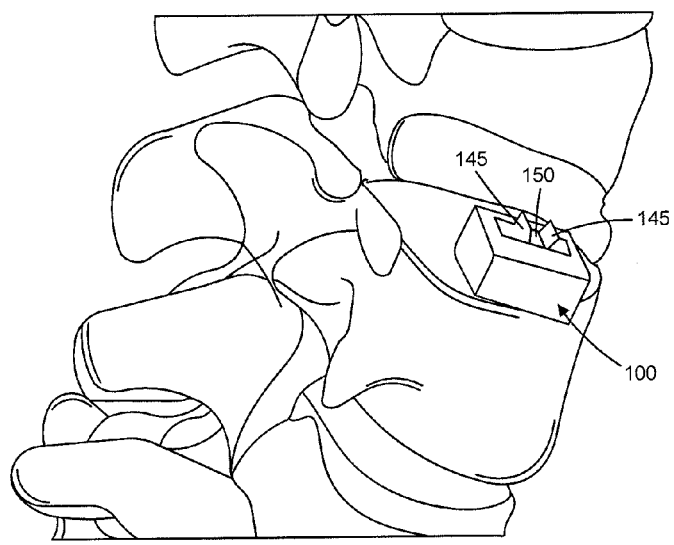
FIG. 4A is a perspective view of an implant positioned within the disc space between a vertebral pair.
Figure 4B:
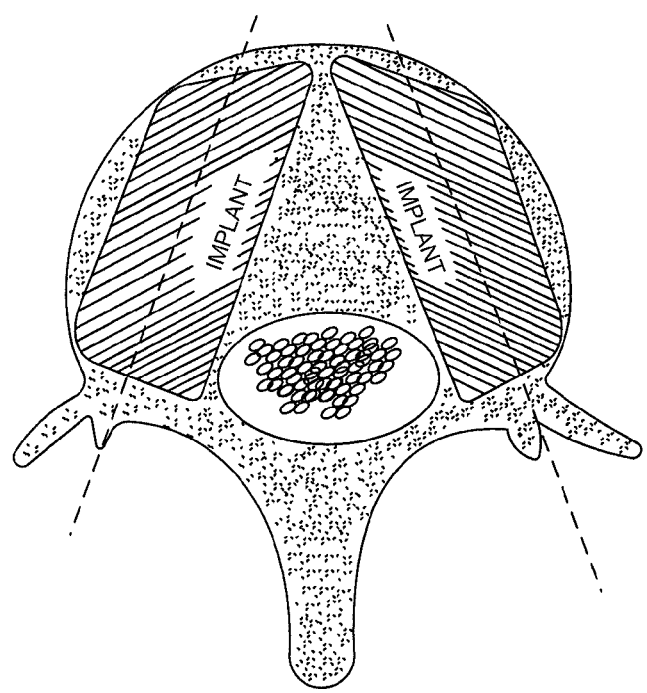
FIG. 4B is a simplified, sectional axial view of a vertebra having two implants deployed thereon.

The implant 100 can be positioned between an inferior and superior vertebra 10, 15 within the intervertebral disc space, for example, vacated after a complete or partial discectomy (see FIGS. 4A-4B). The superior and inferior surfaces 105, 110 can be generally parallel to one another at a selected height dimension or can be at different heights such that the surfaces 105, 110 are generally non-parallel to each other. In addition, the superior and inferior surfaces 105, 110 can be fixed relative to one another or expandable as will be described in more details below. The superior and inferior surfaces 105, 110 can include a one or more fusion slots 135 extending through the full thickness of the surfaces 105, 110 such that the internal volume 130 of the implant 100 can communicate with the endplates of the adjacent vertebrae. The superior and inferior surfaces 105, 110 can also have a texture or raised features 140 to further contact or grate against the respective endplates to encourage bone repair and fusion.

The superior and inferior surfaces 105, 110 of the implant 100 can include one or more fixation members 145 that extend through corresponding apertures 150 in the one or both of the superior and inferior surfaces 105, 110. As will be discussed in more detail below, the fixation members 145 can be deployed to project outward at least in part through the corresponding apertures 150 to engage the endplate of the inferior and superior vertebrae to transfix the implant 100 therebetween. The fixation members 145 can include hooks, screws, cylinders, staples, nails, or other mechanism that can project outward from the surfaces 105, 110 to engage the vertebral endplates of the respective vertebrae. The fixation members 145 can have serrations or other geometry that provides for optimal fixation to bony surfaces.

The shape of the implant can vary, including rectangular, oval, cylindrical, triangular, square, polygonal, u-shaped, semi-circular, elliptical or other shapes. In an example, the implant 100 can have a shape that matches the outer vertebral body configuration to provide optimal support of the endplates. The implants described herein also replace back plate fixation. The dimensions of the implant 100 can vary as well. Similarly, depending on the dimensions of the implant 100 more than a single implant 100 can be deployed within a single disc space. In an example, the implant can be between about 8 mm to about 12 mm in length. In another example, the implant 100 can be between about 8 mm to about 16 mm in length. Further, the implant can be composed of various materials including stainless steel, radiolucent plastics, polymers such as PEEK, and/or relatively inert implantable materials such as titanium and titanium alloys.

The fixation members 145 can project into and penetrate the endplates of the adjacent vertebral bodies. It should be appreciated that the endplates need not be prepared prior to the deployment of the fixation members 145. Alternatively, the endplates can be prepared, such as for example by grating against the surface of one or more of the endplate such as with a distraction device or the implant itself. Alternatively, the endplates can be prepared by drilling one or more corresponding holes into the vertebral body such that the fixation members 145 can project into the previously made holes. It should be appreciated that endplate preparation can be performed by advancing the device and scraping the bone or by advancing a curette through the device as a separate procedural step.

The relative position of the fixation members 145 can vary. The fixation members 145 and their corresponding apertures 150 can be positioned on either side of the vertebral midline M. The fixation members 145 and their corresponding apertures 150 can be positioned generally along a posterior aspect of the superior and inferior surfaces 105, 110 and on either side of the vertebral midline M. The fixation members 145 and their corresponding apertures 150 can also be positioned generally along an anterior aspect of the superior and inferior surfaces 105, 110 of the implant 100 and on either side of the vertebral midline M.

Figure 3B:
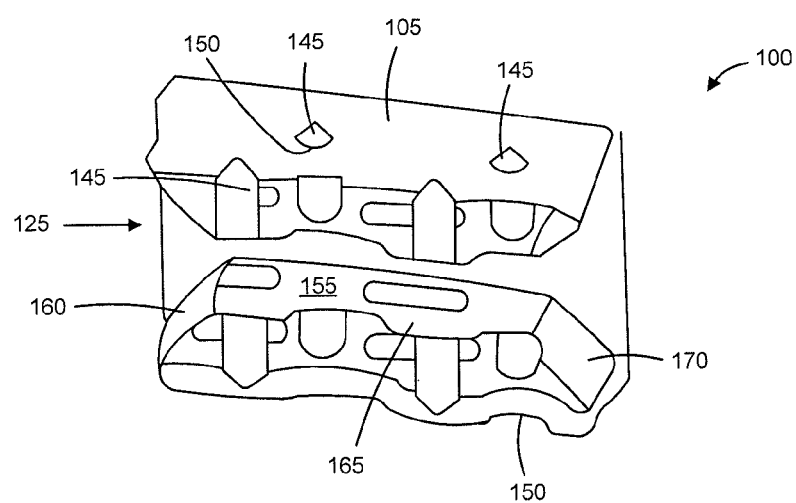
FIG. 3B is a cross-sectional, perspective view of an implant in a pre-deployed state.
Figure 3C:
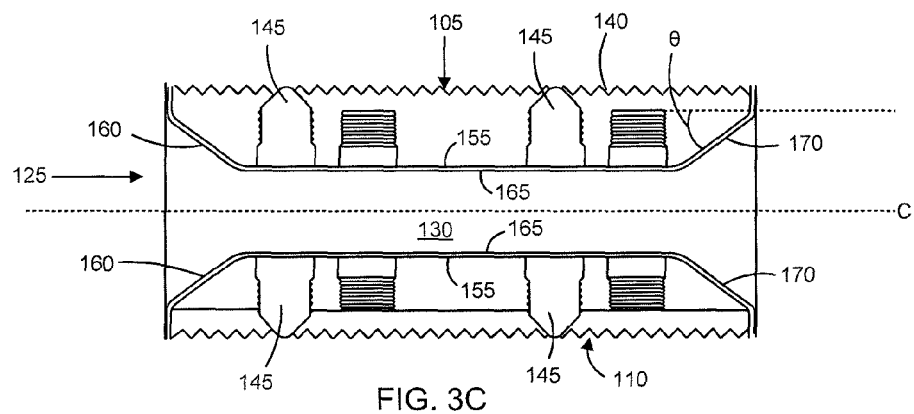
FIG. 3C is a cross-sectional, side view of the implant of FIG. 3B.
Figure 3D:
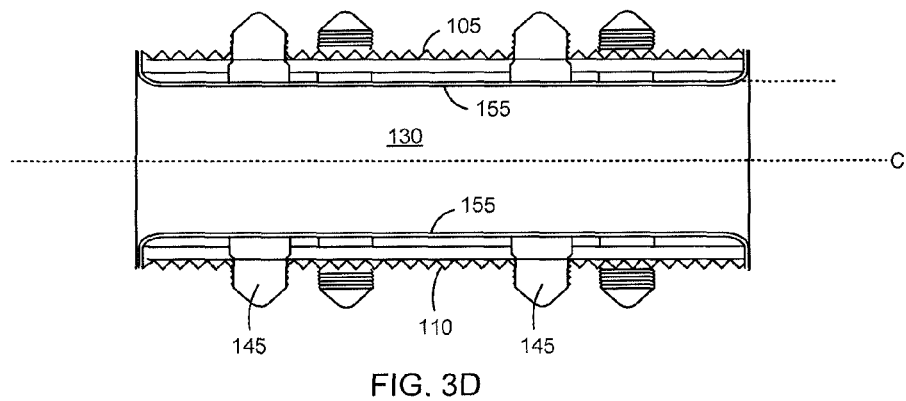
FIG. 3D is a cross-sectional, side view of the implant in a deployed state.

As best shown in the cross-sectional views of FIGS. 3B, 3C and 3D, the fixation members 145 can be coupled to a flexible element or a ramp 155, which in a first, pre-deployed state can project inward toward the internal volume 130 of the implant 100. As such, the fixation members 145 are wholly contained within the implant 100 prior to insertion between the vertebral pair. Deployment of the fixation members 145 can occur through the internal volume 130 of the implant 100 using a deployment device 200, as will be discussed in more detail below. Briefly, the deployment device 200 can engage each of the ramps 155 urging the ramps 155 to move toward their respective superior or inferior surfaces 105, 110 causing at least a portion of the fixation members 145 to extend through the corresponding apertures 150.

The ramps 155 can be made of a relatively thin, flexible material. Each ramp 155 can have a proximal interface 160, a central surface 165 and a distal interface 170. The central surface 165 is positioned between the proximal interface 160 and the distal interface 170 and can be generally parallel to the superior and inferior surfaces 105, 110. In the pre-deployed state as shown in FIGS. 3B and 3C, the proximal interface 160 and the distal interface 170 are angled away from parallel by a first angle such that the ramp 155 projects towards the centerline C of the internal volume 130 of the implant 100. The ramp 155 can be urged from the pre-deployed state towards a flat configuration such as by controlled crimping, bending, or a spring-bias mechanism into a deployed state (see FIG. 3D). In the pre-deployed state, the proximal interface 160 and distal interface 170 project away from the surfaces 105, 110 by a first angle α (see FIG. 3C). As an example, the first angle α can be between about 20 degrees from horizontal to between about 80 degrees from horizontal. Upon deployment, the proximal interface 160 and the distal interface 170 approach the surfaces 105, 110 and can project away from the surfaces 105, 110 by a second angle that is smaller than the first angle (see FIG. 3D). As an example, the second angle can be between about 20 degrees from horizontal to between about 0 degrees from horizontal. This results in at least a portion of the fixation members 145 to extend through the corresponding apertures 150 and engage the adjacent vertebral bodies.

Figure 5A:
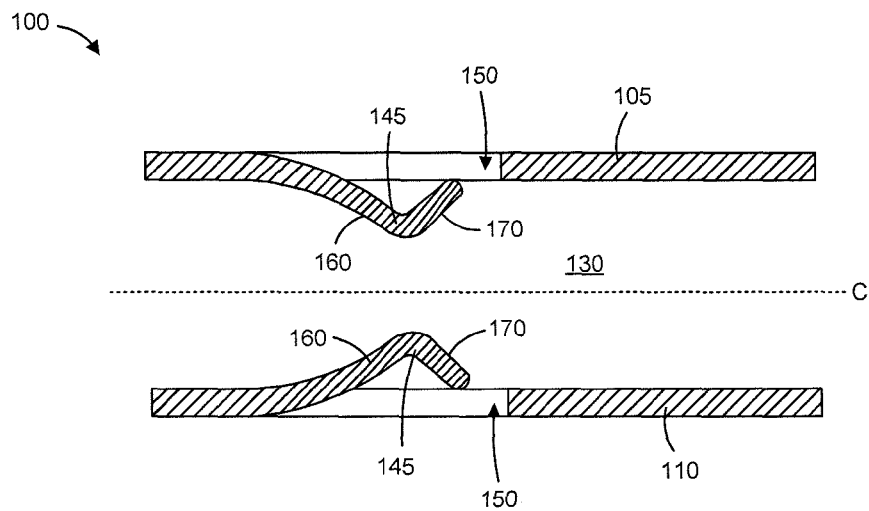
FIG. 5A is a cross-sectional, side view of an implant in a pre-deployed state.
Figure 5B:
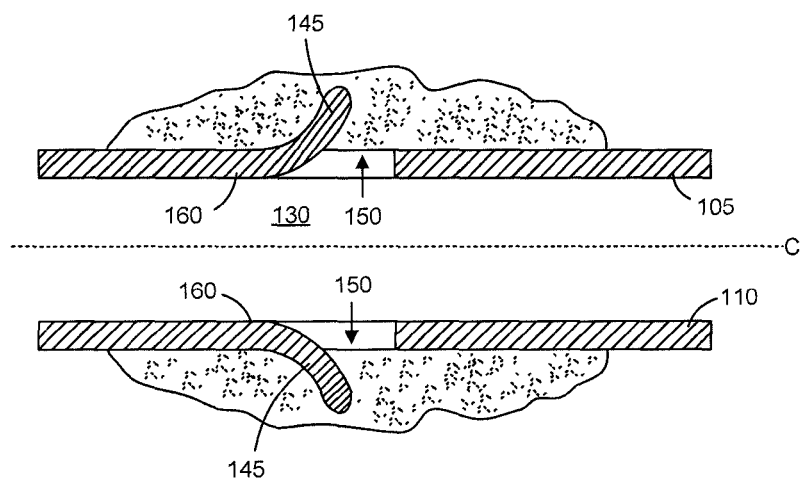
FIG. 5B is a cross-sectional side view of an implant in a deployed state.

FIGS. 5A-5B illustration another variation of the fixation members 145 and their deployment from within the internal volume 130 of the implant 100. In the pre-deployed state, the fixation members 145 are angled towards and wholly contained within the internal volume 130 of the implant 100. In this variation, the fixation members 145 themselves can create the ramp as described above. The fixation members 145 can be a relatively thin, flexible material having a proximal interface 160 and a distal interface 170. In the pre-deployed state as shown in FIG. 5A, the proximal interface 160 and the distal interface 170 are angled away from parallel by a first angle such that the fixation member 145 projects towards the centerline C of the internal volume 130 of the implant 100. The fixation member 145 can be urged from the pre-deployed state towards a deployed state such as by controlled crimping or bending (see FIG. 5B). In the pre-deployed state, the proximal interface 160 and the distal interface 170 project away from the surfaces 105, 110 by at least a first angle. Upon deployment such as by pressing against either the proximal interface 160 or the distal interface 170 with a distal end region 210 of a deployment device 200, the proximal interface 160 approaches the surfaces 105, 110 and projects away from the surfaces 105, 110 by an angle that is smaller than the first angle. This results in at least a portion of the fixation members 145 to extend through the corresponding apertures 150 and engage the adjacent vertebral bodies (see FIG. 5B).

Figure 6A:
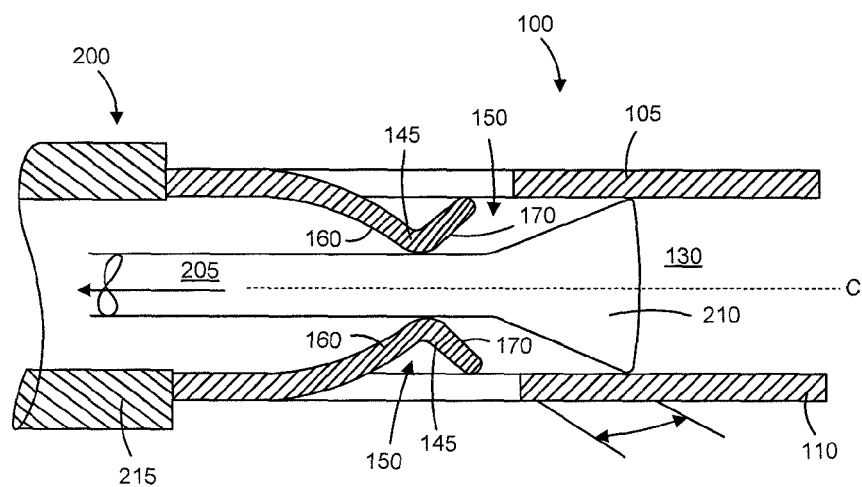
FIG. 6A is a cross-sectional side view of an implant in a pre-deployed state engaged with a deployment device.
Figure 6B:
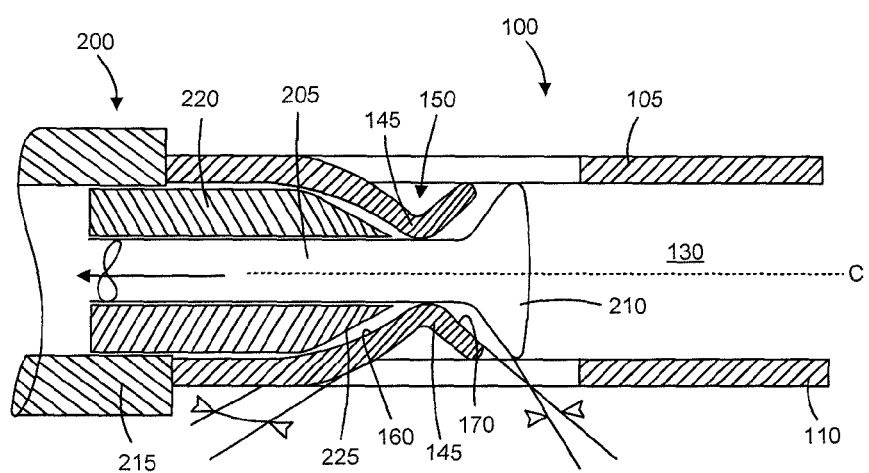
FIG. 6B is a cross-sectional side view of an implant in a pre-deployed state engaged with a deployment device.
Figure 6C:
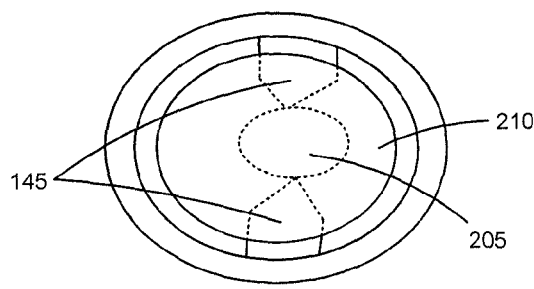
FIG. 6C is a cross-sectional front view of the implant and deployment device of FIG. 6A.

As best shown in FIGS. 6A-6C, the deployment device 200 can include an elongate shaft 205 extending through a delivery cannula 215 and having a distal end region 210 with an enlarged diameter. The implant 100 can be pre-mounted on the distal end region 210. In the pre-mounted version, the distal interface 170 of the fixation member 145 can be engaged by the distal end region 210 of the deployment device 200 upon withdrawal of the elongate shaft 205 from the internal volume 130 of the implant 100. For example, the distal end region 205 of the deployment device 200 can engage the distal interface 170 of the fixation member 145 as the distal end region 210 is withdrawn into the delivery cannula 215. The enlarged outer diameter of the distal end region 210 can press against the distal interface 170 at an angle that urges the fixation member 145 away from the centerline of the internal volume 130 towards either the superior 105 or the inferior surface 110 of the implant 100. In turn, at least a portion of the fixation members 145 project through their corresponding apertures 150 in either the superior 105 or inferior surfaces 110 and penetrate the endplates of the adjacent vertebrae. Alternatively, the distal end region 210 of the deployment device 200 can engage the proximal interface 160 of the fixation member 145 as the distal end region 210 is extended in a distal direction through the delivery cannula 215. The enlarged outer diameter of the distal end region 210 presses against the proximal interface 160 at an angle that urges the fixation member 145 away from the centerline C of the internal volume 130 in an upward and downward direction as described above.

As shown in FIG. 6B, in some aspects the deployment device 200 can also include a deployment safety stop 220. The safety stop 220 can be a tubular element having an internal lumen through which the elongate shaft 205 can move. The safety stop 220 and the shaft 205 can move relative to one another. In a variation, the safety stop 220 is fixed and not moveable and the shaft 205 can be extended distally or withdrawn proximally relative to the safety stop 220. In another variation, the safety stop 220 is not fixed and can move in either a proximal or distal direction or both. The safety stop 220 can have a distal portion 225 that is tapered. The tapered distal portion 225 can have a shape that corresponds generally to the proximal interface 160 of the fixation members 145. During deployment of the fixation members 145 and the withdrawal of the elongate shaft 205 from a distal to a proximal direction, the safety stop 220 can prevent the inadvertent buckling of the fixation member 145 towards the interior volume 130 of the implant 100. Rather, as the elongate shaft 205 is withdrawn and the distal end region 210 presses against the distal interface 170 of the fixation member 145, the safety stop 220 can contact or press against the proximal interface 160 of the fixation member 145 further urging the fixation member to project out through the corresponding apertures 150 in the surfaces 105, 110. It should be appreciated that other coupling mechanisms are considered herein. The above is meant to be an example of a coupling mechanism and is not intended to be limiting.

Following deployment of the fixation members 145, additional fixation elements can be delivered to further fix the deployed implant within the disc space between the vertebrae. For example, surgical staples can be delivered through a trocar to the vertebral endplates for fixation and a staple gun used to further fix the implant. It should also be appreciated that adhesives like calcium phosphate or another bone grown stimulant can be used in combination with the fixation elements described herein to improve fixation of the implant 100 with the adjacent vertebrae.

Once the implant 100 is positioned between the vertebral pair within the intervertebral disc space and the fixation members 145 deployed through corresponding apertures 150 in the superior and inferior surfaces 105, 110 of the implant 100, the internal volume 130 of the implant 100 is relatively hollow and available for implantation of material such as bone graft material or osteoconductive healing material or bone growth stimulating material. Despite the open design of the implant 100, the superior and inferior surfaces 105, 110 still provide a relatively large surface area for the vertebral endplates to contact for healing to occur. Autologous disc material can be injected through the opening 125 to enhance healing while creating fusion. The fusion slots 135 (see FIG. 3A) and apertures 150 create an open design of the implant 100 allowing for material injected into the internal volume 130 to communicate, migrate and improve fusion between the implant 100 and the adjacent bony surfaces.

The implant 100 can be provided in a kit with one or more delivery devices. For example, the implant 100 can be provided in a kid in a pre-deployed state with a delivery device pre-loaded therein. In a further example, the implant 100 can be provided in a kit along with an access device for the dilation, retraction and delivery of the implant 100. The kit can also be packaged with instructions for use and in a format convenient for surgical operating rooms, for example, in a box or in a sterile plastic wrapping or pouch, which can be sealed and sterilized. Different types of kits are contemplated herein and can be tailored to meet the needs of a particular surgical method.

Method of Use

It should be appreciated that implants described herein can be inserted in a variety of approaches including posterior, lateral, anterior and posterior lateral approaches. The procedures described herein can be performed uni-laterally or bi-laterally. The approach can be posterior lateral and the devices can be advanced through Kambin's Triangle.

Generally, the patient can be in a prone position and under anesthesia that can be intravenous sedation, local, or general anesthesia. Wilson frames or pillows can be used under the patient's stomach to "open up" the spine/disc space. The frames/pillows can be repositioned or removed throughout various steps of the procedure in order to "open up" other portions of the patient's spine. For example, if the anterior part of the spine needs to be "opened up" the pillows/frames may be removed or repositioned.

A surgeon can create an incision in the back of a patient through which a trocar can be advanced over a wire through Kambin's triangle. The trocar can be advanced up to and/or into the disc space. An access device (not shown) can be advanced over or through the trocar and positioned through Kambin's triangle and into the disc space. The access device and other components related to dilation, distraction and delivery of tools and materials to the disc space are described in co-pending application Ser. No. 13/371,141, entitled "Delivery Device With Interior Dilation Element Channel," filed on the same day herewith, and which is incorporated by reference in its entirety.

At this stage, a full or partial discectomy can be performed according to methods known in the art. The access device can be expanded by sequentially advancing dilator tubes through the interior lumen of the access device. Each of the dilator tubes has an outer diameter that is larger than the previously inserted dilator tube such that they gradually separate the opposing halves of the access device. As the access device expands, the opposing halves press against adjacent tissues creating an access channel to the disc space. Further, the expansion of the access device near the distal end presses against the superior and inferior vertebrae 10, 15 causing distraction of the vertebrae away from one another to achieve an optimal disc height. As such the access device can both dilate and distract tissues.

Once the optimal position and disc height is achieved, one or more implants 100 can be delivered through the access device and deployed within the disc space. The endplate 47 of each vertebrae 10, 15 can be prepared prior to implant 100 delivery to improve fusion of the bones with the implant, such as by contacting the distal end of the access device against the endplates. The vertebrae 10, 15 can be prepared for fusion by scraping, breaking through, or cutting into, the endplates to allow the interposed bone graft to come into direct contact with the more vascular cancellous (spongy) bone, and to thereby urge the body to heal this induced and controlled injury to the bone such that the superior and inferior vertebrae 10, 15 become one continuous segment of bone.

Once the implant 100 is appropriately positioned between the vertebral pair, a deployment device 200 can be withdrawn from the proximal opening 125 in the implant 100 to deploy the fixation elements 145 of the implant 100 into the vertebral endplates as described above. The implant 100 can be further fixated using staples, screws, adhesives and other fixation devices as is known in the art. Once fixed in place, the internal volume 130 implant 100 can be filled with material to further encourage bone regrowth and healing. As an example, a surgeon can inject bone graft or bone growth stimulants following the discectomy into the internal volume 130 of the implant 100. The proximal and distal regions of the implant 100 can be capped to prevent inadvertent migration of the injected material. Other materials can be injected as well including bone graft, allograft or osteoconductive material. The success of the steps can be confirmed by fluoroscopy prior to removal of tools and closure of the incision.

While this specification contains many specifics, these should not be construed as limitations on the scope of what is claimed or of what may be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or a variation of a sub-combination. Similarly, while operations are depicted in the drawings in a particular order, this should not be understood as requiring that such operations be performed in the particular order shown or in sequential order, or that all illustrated operations be performed, to achieve desirable results. Only a few examples and implementations are disclosed. Variations, modifications and enhancements to the described examples and implementations and other implementations may be made based on what is disclosed.

What is claimed is:

1. An intervertebral fixation device, comprising:
   a housing sized to be positioned between adjacent inferior and superior vertebrae, the housing comprising an internal volume defined by an inferior coupling element, a superior coupling element, and first and second sidewalls, wherein the internal volume comprises a longitudinal axis extending between the inferior coupling element and the superior coupling element and extending through the first and second sidewalls;
   at least one flexible element coupled to an internal surface of at least one of the inferior or superior coupling elements, wherein the at least one flexible element projects inward toward the longitudinal axis of the internal volume of the housing when in a first configuration and projects outward away from the longitudinal axis of the internal volume toward the internal surface to which the at least one flexible element is coupled when in a second configuration; and
   at least one fixation member coupled to the flexible element and sized to extend through a corresponding aperture in the inferior or superior coupling element.

2. The device of claim 1, wherein the fixation member is wholly contained within the internal volume of the housing when the flexible element is in the first configuration.

3. The device of claim 1, wherein the fixation member extends at least in part through the aperture when the flexible element is in the second configuration.

4. The device of claim 3, wherein the fixation member projects into an adjacent endplate when the flexible element is in the second configuration.

5. The device of claim 1, further comprising a plurality of flexible elements.

6. The device of claim 1, further comprising a plurality of fixation members.

7. The device of claim 1, wherein the inferior and superior coupling elements are parallel to one another.

8. The device of claim 1, wherein the inferior and superior coupling elements are non-parallel to one another.

9. The device of claim 1, wherein at least one of the inferior and superior coupling elements comprises a textured outer surface.

10. The device of claim 1, wherein the housing further comprises a proximal opening through which the internal volume is accessible.

11. The device of claim 10, further comprising a delivery device having a distal end region configured to extend into the internal volume through the proximal opening and couple to the housing.

12. The device of claim 11, wherein the flexible element is deployed using the delivery device extending through the proximal opening.

13. A method of treating a spinal disorder in a patient with an intervertebral fixation device, comprising:
- accessing a disc space between an inferior vertebra and a superior vertebra;
- advancing an intervertebral fixation device positioned on a delivery device into the disc space between the inferior and superior vertebrae, the intervertebral fixation device comprising:
  - a housing comprising an internal volume defined by an inferior coupling element, a superior coupling element, and first and second sidewalls, wherein the internal volume comprises a longitudinal axis extending between the inferior coupling element and the superior coupling element and extending through the first and second sidewalls;
  - at least one flexible element coupled to an internal surface of at least one of the inferior or superior coupling elements, wherein the at least one flexible element projects inward toward the longitudinal axis of the internal volume of the housing when in a first configuration and projects outward away from the longitudinal axis of the internal volume toward the internal surface to which the at least one flexible element is coupled when in a second configuration; and
  - at least one fixation member coupled to the flexible element and sized to extend through a corresponding aperture in the inferior or superior coupling element; and
- deploying the at least one flexible element to the second configuration with the delivery device such that the fixation member extends at least in part through the aperture.

14. The method of claim 13, wherein accessing a disc space between an inferior vertebra and a superior vertebra comprises inserting an access device through Kambin's triangle into the disc space.

15. The method of claim 14, further comprising using the access device to prepare a vertebral endplate of the inferior or the superior vertebrae.

16. The method of claim 15, wherein advancing an intervertebral fixation device positioned on a delivery device comprises inserting the intervertebral fixation device through the access device into the disc space.

17. The method of claim 13, wherein the fixation member is wholly contained within the internal volume of the housing when the flexible element is in the first configuration.

18. The method of claim 13, wherein the fixation member projects into a vertebral endplate of the inferior or the superior vertebrae when the flexible element is in the second configuration.

19. The method of claim 13, wherein the housing further comprises a proximal opening through which at least a distal end region of the delivery device can extend into the internal volume.

20. The method of claim 19, wherein deploying the at least one flexible element comprises withdrawing in a proximal direction the delivery device from the internal volume through the proximal opening.

21. The method of claim 20, wherein the distal end region of the delivery device comprises a flange that presses against the flexible element urging the fixation member through the aperture when the delivery device is withdrawn in the proximal direction.

22. The method of claim 19, further comprising injecting bone growth stimulating material into the internal volume of the housing through the proximal opening.

23. The method of claim 13, wherein the intervertebral fixation device further comprises a plurality of flexible elements.

24. The method of claim 13, wherein the intervertebral fixation device further comprises a plurality of fixation members.

25. A kit for use in treating a spinal disorder, comprising:
- an intervertebral fixation device, comprising:
  - a housing sized to be positioned between adjacent inferior and superior vertebrae, the housing comprising a proximal opening to an internal volume defined by an inferior coupling element, a superior coupling element, and first and second sidewalls, wherein the internal volume comprises a longitudinal axis extending between the inferior coupling element and the superior coupling element and extending through the first and second sidewalls;
  - at least one flexible element coupled to an internal surface of at least one of the inferior or superior coupling elements, wherein the at least one flexible element projects inward toward the longitudinal axis of the internal volume of the housing when in a first configuration and projects outward away from the longitudinal axis of the internal volume toward the internal surface to which the at least one flexible element is coupled when in a second configuration; and
  - at least one fixation member coupled to the flexible element and sized to extend through a corresponding aperture in the inferior or superior coupling element; and
- a delivery device comprising a proximal, elongate portion and a distal end region, wherein the distal end region is configured to extend into the internal volume through the proximal opening and couple to the housing.

26. The kit of claim 25, wherein the delivery device is pre-coupled to the intervertebral fixation device.

27. The kit of claim 25, further comprising bone growth stimulating material.

28. The kit of claim 25, further comprising an access and distraction device, wherein the intervertebral fixation device is configured to be delivered through a working channel of the access and distraction device.

* * * * *